(12) United States Patent
Chrysanthakopoulos

(10) Patent No.: US 12,324,851 B2
(45) Date of Patent: Jun. 10, 2025

(54) DRAWING SUBSTRATE

(71) Applicant: BIC Violex Single Member S.A., Anoixi (GR)

(72) Inventor: Nikolaos Chrysanthakopoulos, Anoixi (GR)

(73) Assignee: BIC Violex Single Member S.A., Anoixi (GR)

( * ) Notice: Subject to any disclaimer, the term of this patent is extended or adjusted under 35 U.S.C. 154(b) by 0 days.

(21) Appl. No.: 18/325,820

(22) Filed: May 30, 2023

(65) Prior Publication Data

US 2023/0381089 A1  Nov. 30, 2023

(51) Int. Cl.
*B32B 3/10* (2006.01)
*A61K 8/02* (2006.01)
*A61K 8/9783* (2017.01)
*B44D 2/00* (2006.01)

(52) U.S. Cl.
CPC .......... *A61K 8/9783* (2017.08); *A61K 8/0208* (2013.01); *B44D 2/002* (2013.01); *A61K 2800/43* (2013.01)

(58) Field of Classification Search
None
See application file for complete search history.

(56) References Cited

U.S. PATENT DOCUMENTS

| | | | |
|---|---|---|---|
| 4,169,169 A | 9/1979 | Kitabatake | |
| 6,106,852 A | 8/2000 | Vineberg | |
| 6,192,890 B1 | 2/2001 | Levy et al. | |
| 7,699,917 B1 | 4/2010 | Pagnotta | |
| 10,722,160 B2 | 7/2020 | Wang et al. | |
| 11,064,946 B2 | 7/2021 | Rogers et al. | |
| 2008/0274308 A1 | 11/2008 | Lu | |
| 2009/0325221 A1 | 12/2009 | Long et al. | |
| 2017/0071536 A1 | 3/2017 | Tibbits et al. | |

FOREIGN PATENT DOCUMENTS

| | | | |
|---|---|---|---|
| CN | 1966589 A | * | 5/2007 |
| CN | 111253206 A | * | 6/2020 |
| JP | 02172468 A | * | 7/1990 |
| JP | 2004252291 A | * | 9/2004 |
| KR | 20100098867 A | | 9/2010 |
| KR | 101255378 B1 | | 4/2013 |
| WO | 9413491 A1 | | 6/1994 |
| WO | 2002076379 A2 | | 10/2002 |

(Continued)

OTHER PUBLICATIONS

Machine translation of JP-02172468-A (Year: 1990).*

(Continued)

*Primary Examiner* — Christopher M Polley
(74) *Attorney, Agent, or Firm* — Bookoff McAndrews, PLLC

(57) ABSTRACT

In a first aspect, the present disclosure relates to a substrate 100 comprising an adhesive, a hygroexpansible material 110 and a hygroinert ink 120. In a second aspect, the present disclosure relates to a system comprising: a substrate 100 comprising a hygroexpansible material 110 and an adhesive. Further the system according to the second aspect comprises a writing instrument comprising an ink cartridge comprising a hygroinert ink 120.

17 Claims, 3 Drawing Sheets

(56) References Cited

FOREIGN PATENT DOCUMENTS

| | | |
|---|---|---|
| WO | 03031531 A1 | 4/2003 |
| WO | 2018144627 A1 | 8/2018 |

OTHER PUBLICATIONS

Machine translation of JP-2004252291-A (Year: 2004).*
Machine translation of CN-1966589-A (Year: 2007).*
Machine translation of CN-111253206-A (Year: 2020).*
Kruss https://www.kruss-scientific.com/en-US/know-how/use-cases/offset-printing#:~:text=The%20ink%20exhibits%20the%20opposite,having%20a%20low%20surface%20polarity. (Year: 2021).*
He X., Flexible and Superwettable Bands as a Platform toward Sweat Sampling and Sensing, ACS Appl. Polym. Mater. 2020, 2, 5, 2055-2062, Publication Date: Apr. 10, 2020, https://doi.org/10.1021/acsapm.0c00213, Copyright © 2020 American Chemical Society.
Colaco, R. et al., Mechanochromic Microfibers Stabilized by Polymer Blending, Anal. Chem. 2019, 91, 7, 4296-4300, Publication Date: Mar. 18, 2019, https://doi.org/10.1021/acs.analchem.8b05875.
European Search Report issued in European Application No. 22176489.7, mailed on Feb. 2, 2023.
Jurewicz, I., King, A. A. K., Shanker, R., Large, M. J., Smith, R. J., Maspero, R., Ogilvie, S. P., Scheerder, J., Han, J., Backes, C., Razal, J. M., Florescu, M., Keddie, J. L., Coleman, J. N., Dalton, A. B., Mechanochromic and Thermochromic Sensors Based on Graphene Infused Polymer Opals. Adv. Funct. Mater. 2020, 30, 2002473. https://doi.org/10.1002/adfm.202002473.
Nina Notman, Smart Tattoos, Mar. 29, 2021, © Royal Society of Chemistry 2023, Source: © Gary Neill, https://www.chemistryworld.com/features/smart-tattoos-are-keeping-tabs-on-our-health/4013366.article.
Unger, K., Greco, F., Coclite, A. M., Temporary Tattoo pH Sensor with pH-Responsive Hydrogel via Initiated Chemical Vapor Deposition. Adv. Mater. Technol. 2022, 7, 2100717. https://doi.org/10.1002/admt.202100717.
Wang L, Zhou W, Tang Q, Yang H, Zhou Q, Zhang X. Rhodamine-Functionalized Mechanochromic and Mechanofluorescent Hydrogels with Enhanced Mechanoresponsive Sensitivity. Polymers. 2018; 10(9):994. https://doi.org/10.3390/polym10090994.

* cited by examiner

DRAWING SUBSTRATE

This application claims priority from the European Patent Application No. 22176489.7, filed on May 31, 2022, its content being incorporated herein by reference.

TECHNICAL FIELD

The present disclosure relates to the field of stickers. More specifically, the present disclosure relates to stickers exhibiting hygromorphic action.

BACKGROUND

A sticker is usually a printed product made of paper or plastic. The print is applied to one surface and a second surface is adhesive. The second surface allows attaching the sticker to a variety of surfaces.

Stickers are used for a variety of purposes. Stickers may be used as advertising media, product identifications or as official identification media, for example country stickers on number plates.

Another use of stickers is body ornamentation. For example, stickers, in particular peel-away stickers, may be attached to skin as a temporary tattoo. The last developments of stickers configured to be used as temporary tattoos have been primarily focused on durability of the stickers. For example, peel-away stickers which are last longer on the skin or may only be removed by the use of alcohol have been developed. However, manufacturers of stickers are still limited to only static images.

The present disclosure relates to improved stickers comprising novel technical features to allow the provision of innovative designs.

SUMMARY

In a first aspect, the present disclosure relates to a substrate comprising an adhesive, a hygroexpansible material and a hygroinert ink.

In a second aspect, the present disclosure relates to a system comprising: a substrate comprising a hygroexpansible material and an adhesive. Further the system according to the second aspect comprises a writing instrument comprising an ink cartridge comprising a hygroinert ink.

In some embodiments, the hygroexpansible material may be configured to swell more compared to the hygroinert ink.

In some embodiments, the hygroexpansible material may be configured to swell and the hygroinert ink may be configured not to swell.

In some embodiments, the hygroexpansible material may be hydrophilic and the hygroinert ink may be hydrophobic.

In some embodiments, the hygroexpansible material may form a hygroexpansible layer and the hygroinert ink may form a hygroinert layer, wherein the hygroinert layer may be disposed at least on a part of the hygroexpansible layer.

In some embodiments, the hygroinert ink may cover between about 0.5% to about 100%, more specifically 1% to about 99%, even more specifically between about 5% to about 75% and in particular between about 20% to about 60% of the hygroexpansible material's 110 or hygroexpansible layer's surface.

In some embodiments, the hygroexpansible material may comprise a sporopollenin.

In some embodiments, the hygroexpansible material may comprise pollen paper.

In some embodiments, the hygroexpansible material may have a young's modulus between about 90 to about 1200 MPa.

In some embodiments, the hygroinert ink may have a young's modulus between about 5000 to about 20000, more specifically between about 10000 to about 12000, when dry.

In some embodiments, the substrate may have a thickness between about 5 µm to about 1000 µm, more specifically between about 10 µm to about 100 µm.

In some embodiments, the substrate may have a diameter of between about 1 cm to about 100 cm.

In some embodiments, the substrate may comprise a first section comprising the adhesive and a second section attached to the first section.

In some embodiments, the first section may be attached to the second section in an attachment area.

In some embodiments, the second section may not comprise the adhesive.

In some embodiments, the second section may comprise a free end.

In some embodiments, the second section may be a free end.

In some embodiments, the hygroexpansible material may be configured to expand in at least one direction from about 0.4% to about 1.6%, when the water content within the hygroexpansible material is increased from about 20 wt.-% to about 70 wt.-%.

In some embodiments, the substrate may have a deformability between about 0.02/cm*%-relative air humidity to about 0.25/cm*%-relative air humidity.

In some embodiments, the substrate may have a deformability between about 0.02/cm*water content wt.-% to about 0.25/cm*water content wt.-%, wherein the water content is relative to the maximum water absorption capacity of the hygroexpansible material.

In some embodiments, the substrate may exhibit an increase of the maximum bending curvature of between about 1.0 $cm^{-1}$ to about 5.0 $cm^{-1}$, more specifically of between about 2.0 $cm^{-1}$ to about 4.0 $cm^{-1}$, and in particular of between about 2.5 $cm^{-1}$ to about 3.5 $cm^{-1}$, when a water content within the hygroexpansible material is increased from about 20 wt.-% to about 100 wt.-%, relative to the maximum water absorption capacity of the hygroexpansible material.

In some embodiments, the substrate may exhibit an increase of the maximum bending curvature from about 0.10 $cm^{-1}$ to about 3.1 $cm^{-1}$ when the water content within the hygroexpansible material is increased from about 20 wt.-% to about 100 wt.-%, relative to the maximum water absorption capacity of the hygroexpansible material.

In some embodiments, the hygroinert ink may be configured to seal the hygroexpansible material from a solvent, in particular water.

In some embodiments, the hygroinert ink may form at least one hygroinert ink layer, in particular wherein the hygroinert ink layer is configured to absorb tensile forces.

In some embodiments, the hygroinert ink may comprise a first polymer, more specifically a hydrocarbon polymer and in particular an aromatic hydrocarbon polymer.

In some embodiments, the first polymer may comprise styrene, more specifically the hygroinert ink may comprise a styrene acrylate copolymer and/or polystyrene.

In some embodiments, the hygroexpansible material may comprise a sporopollenin, more specifically pollen paper, and the hygroinert ink may comprise an aromatic hydrocarbon polymer, more specifically a styrene acrylate copolymer and/or polystyrene.

In some embodiments, the nk may comprise between about 10 wt.-% to about 100 wt.-%, more specifically between about 25 wt.-% to about 75 wt.-% and in particular between about 40 wt.-% to about 60 wt.-% of the first polymer.

In some embodiments, the hygroinert ink may comprise alkyl ketene, in particular the hygroinert ink may comprise between about 10 wt.-% to about 100 wt.-%, more specifically between about 25 wt.-% to about 75 wt.-% and in particular between about 40 wt.-% to about 60 wt.-% of the alkyl ketene dimer.

In some embodiments, the hygroinert ink may comprise p-xylene, in particular the hygroinert ink may comprise between about 10 wt.-% to about 99 wt.%, more specifically between about 25 wt.-% to about 75 wt.-% and in particular between about 40 wt.-% to about 60 wt.-% of p-xylene.

In some embodiments, the hygroinert ink may comprise between about 2 wt.-% to about 90 wt.-%, more specifically between about 5 wt.-% to about 50 wt.-% and in particular between about 10 wt.-% to about 20 wt.-% of one or more waxes.

In some embodiments, the hygroinert ink may have a thickness between about 0.5 μm μm to about 50 μm, more specifically between about 2 μm to about 15 μm.

In some embodiments, the hygroinert ink may form one or more lines, wherein the one or more lines have a width between about 0.01 mm to about 10 mm, more specifically between about 0.1 mm to about 5 mm.

In some embodiments, the substrate may comprise a mechanochromic material, in particular in the form of a mechanochromic layer.

In some embodiments, the mechanochromic material may comprise mechanochromic fibers, in particular mechanochromic polymer fibers.

In some embodiments, the mechanochromic layer may have a thickness between about 1 μm to about 2000 μm, more specifically between about 5 μm to about 400 μm, and in particular between about 10 μm to about 200 μm.

In some embodiments, the mechanochromic material may comprise a photonic material, a piezophotonic material, a microcrack structure material and/or a mechanophore, in particular a mechanophore-linked polymer.

In some embodiments, the mechanophore may be configured to undergo a ring-opening under mechanical stress, more specifically a reversible ring-opening under mechanical stress and in particular to transform from a spirocyclic form to a ring-opened form under mechanical stress.

In some embodiments, the mechanochromic material may comprise a mechanochromic polymer, more specifically a mechanochromic polymer comprising a rhodamine and in particular a mechanochromic rhodamine spirolactam micellar hydrogel.

In some embodiments, the mechanochromic material may comprise spheres, more specifically the spheres may be polymer spheres and in particular the polymer spheres may comprise a copolymer of methyl methacrylate, butyl acrylate and methacrylic acid.

In some embodiments, the mechanochromic material may comprise a latex, more specifically the latex may comprise the polymer spheres and in particular the latex may comprise the polymer spheres and graphene.

In some embodiments, the polymer spheres may have a size between about 100 nm to about 400 nm, more specifically between about 200 nm to about 300 nm.

In some embodiments, the mechanochromic material may have a graphene content between about 0.001 wt.-% to about 0.1 wt.-%, more specifically between about 0.005 to about 0.02 wt.-% relative to the total weight of the polymer spheres.

In some embodiments, the latex may have a water content between about 1 wt.-% to about 30 wt.-%, more specifically between about 5 wt.-% to about wt.-% and in particular between about 8 wt.-% to about 12 wt.-%, relative to the total weight of the latex.

In some embodiments, the mechanochromic material may comprise silica particles and poly(ethylene glycol) phenyl ether acrylate rubber.

In some embodiments, the mechanochromic material may comprise polystyrene spheres, at least one aligned carbon nanotubes sheet and PDMS fibers.

In some embodiments, the mechanochromic material may comprise poly(butyl acrylate) spheres, 2-ethylhexyl acrylate and a polyacrylic acid hydrogel.

In some embodiments, the color change of the mechanochromic material may be reversible.

In some embodiments, the mechanochromic material may be configured to change color when exposed to a mechanical force between about 0.1 N to about 5 N.

In some embodiments, the mechanochromic material may be configured to change color when stretched by between about 50% to about 500%.

In some embodiments, the mechanochromic material may be configured to change color when exposed to a mechanical force between about 0.3 MPa to about 3 MPa.

In some embodiments, the adhesive may be comprised within an adhesive layer.

In some embodiments, the adhesive may be safe for human use.

In some embodiments, the adhesive may be configured to be a removable adhesive.

In some embodiments, the adhesive may comprise a second polymer, in particular an acrylic, a rubber and/or a silicon.

In some embodiments, the adhesive may be attached to a detachable layer, more specifically a detachable layer comprising a third polymer and in particular a detachable layer comprising cellulose paper, polypropylene and/or polyester.

In some embodiments, the substrate may comprise a sealant layer, more specifically a sealant layer configured to prevent water from passing therethrough.

In some embodiments, the sealant may comprise a fourth polymer, more specifically the sealant may comprise a biopolymer, and in particular the sealant may comprise chitosan.

In some embodiments, the substrate may comprise a base layer, more specifically the base layer may comprise a polymer and/or paper, and in particular a biopolymer and/or cellulose paper.

In some embodiments, the substrate may comprise a water-absorbing material, in particular a hydrogel.

In some embodiments, the substrate may comprise a middle layer attached to a top and a bottom layer, wherein the top layer is the sealant layer, the middle layer comprises the hygroexpansible material and the hygroinert ink and the bottom layer comprises the adhesive.

In some embodiments, the substrate additionally may comprise the detachable layer attached to the bottom layer and the base layer arranged between bottom layer and the middle layer.

In some embodiments, the substrate may be a peel-away sticker.

In some embodiments, the substrate may be configured to be attached to skin.

In a third aspect, the present disclosure relates to a method for manufacturing a substrate, wherein the method comprises adding an adhesive layer to a hygroexpansible material, in particular pollen paper. The process according to the third aspect may optionally comprise printing a pattern on the pollen paper with hygroinert ink.

In some embodiments, the process according to the third aspect comprises attaching a detachable layer to the adhesive layer and/or coating or attaching a sealant onto the pollen paper.

In a fourth aspect, the present disclosure relates to a kit comprising the substrate or system according to any preceding embodiment, wherein the kit additionally comprises a water-spraying mechanism.

In a fifth aspect, the present disclosure relates to a use of the substrate or system according to any preceding embodiment, wherein the substrate is attached to skin.

In a sixth aspect, the present disclosure relates to a writing instrument according to any preceding embodiment.

An ink cartridge, wherein the ink cartridge comprises an ink as defined in any preceding embodiment, wherein the ink cartridge is configured to be inserted into the writing instrument or a printer.

BRIEF DESCRIPTION OF THE DRAWINGS

Other characteristics will be apparent from the accompanying drawings, which form a part of this disclosure. The drawings are intended to further explain the present disclosure and to enable a person skilled in the art to practice it. However, the drawings are intended as non-limiting embodiments. Common reference numerals on different Figures indicate like or similar features.

DETAILED DESCRIPTION

Figure 1B:
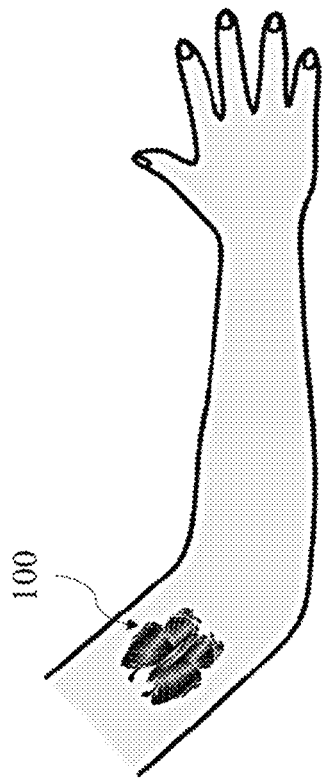
FIG. 1B shows a substrate according to the first aspect in a wet state attached to an arm.

Hereinafter, a detailed description will be given of the present disclosure. The terms or words used in the description and the aspects of the present disclosure are not to be construed limitedly as only having common-language or dictionary meanings and should, unless specifically defined otherwise in the following description, be interpreted as having their ordinary technical meaning as established in the relevant technical field. The detailed description will refer to specific embodiments to better illustrate the present disclosure, however, it should be understood that the presented disclosure is not limited to these specific embodiments.

In a first aspect, the present disclosure relates to a substrate 100 comprising an adhesive, a hygroexpansible material 110 and a hygroinert ink 120.

The term "hygroexpansible material 110" within this disclosure i.a. to its common meaning in the art. Additionally or alternatively, the term "hygroexpansible material 110" may refer to a material configured to absorb water and/or to increase its volume when absorbing water. Additionally or alternatively, the term "hygroexpansible material 110" within this disclosure may refer to a material configured to absorb up to at least 10 wt.-%, more specifically up to at least 30 wt.-% and in particular up to at least 70 wt.-% water, relative to the total weight of the hygroexpansible material 110 including the water and to increase its volume when absorbing water by at least 0.1% per 1 wt.-% water, more specifically at least 0.3% per 1 wt.-% water and in particular at least 0.5% per 1 wt.-% water, wherein the water content is measured relative to the total weight of the hygroexpansible material 110. The absorption of water and/or increase in volume when absorbing water may be reversible.

The term "hygroinert material" within this disclosure i.a. to its common meaning in the art. Additionally or alternatively, the term "hygroinert material" within this disclosure may refer to a material configured to not absorb water. Additionally or alternatively, the term "hygroinert material" may refer to a material configured to absorb less than 5% wt.-%, more specifically less than 1 wt.-% and in particular less than 0.1 wt.-% water, relative to the total weight of the hygroinert material. Additionally or alternatively, the term "hygroinert material" may refer to a material configured to prevent water from passing therethrough.

As outlined above, the hygroexpansible material 110 may be configured to swell more compared to the hygroinert ink 120. The hygroexpansible material 110 may be configured to swell and the hygroinert ink 120 may be configured not to swell. The hygroexpansible material 110 may be hydrophilic and the hygroinert ink 120 may be hydrophobic.

The hygroexpansible material 110 and the hygroinert ink 120 may form a hygromorphic actuator. The geometry of the substrate 100 may be influenced by the hygromorphic actuator or the substrate 100 may be regarded as the hygromorphic actuator itself. The term "hygromorphic actuator" within this disclosure may refer to a structure configured to change its geometry based on a water content within the material. Additionally or alternatively, the term "hygromorphic actuator" may refer to a structure configured to change its geometry based on a relative humidity in ambient air. Additionally or alternatively, the term "hygromorphic actuator" may refer to a structure configured to change its curvature based on the water content within the structure or parts thereof and/or the relative humidity in ambient air. The change in geometry and/or curvature due to a change in water content in the structure and/or relative humidity in ambient air, may also be referred as hygromorphic action. The hygromorphic action may be in particular reversible. The mechanism of the hygromorphic actuator will be outlined in more detail below.

In a second aspect, the present disclosure relates to a system comprising: a substrate 100 comprising a hygroexpansible material 110 and an adhesive. Further the system according to the second aspect comprises a writing instrument comprising an ink cartridge comprising a hygroinert ink 120.

A user may use the writing instrument to draw on the substrate 100 comprising the hygroexpansible material 110. Similar to the first aspect, the hygroinert ink deposited on the substrate 100 may form a hygromorphic actuator together with the hygroexpansible material 110.

The following embodiments relate to the first and second aspect. Properties described for the ink, refer to the properties of the ink when the ink has dried, in particular when the ink has dried on the substrate 100 or hygroexpansible material 110 comprised therein.

Figure 2A:
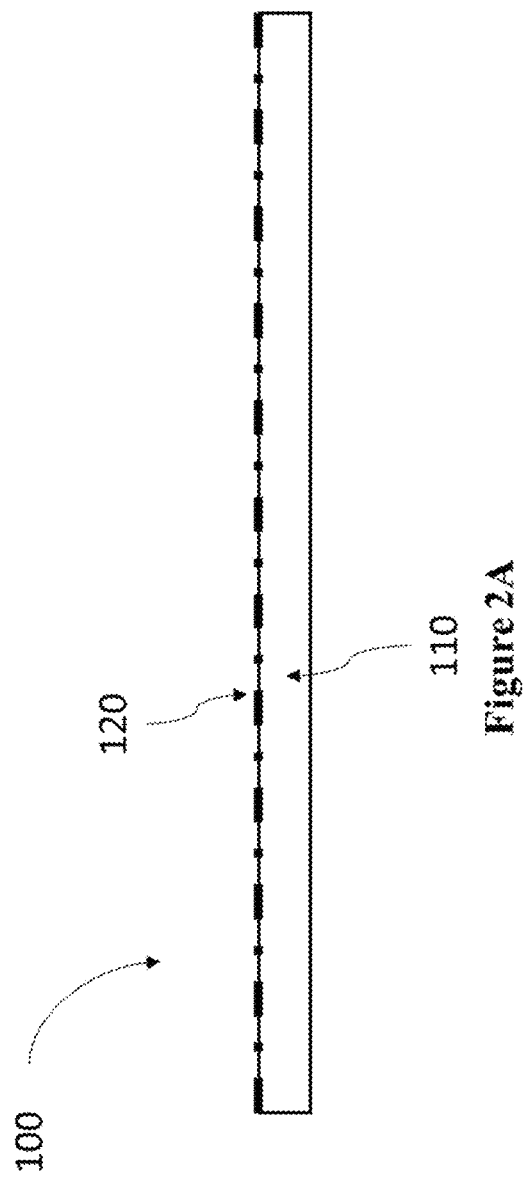
FIG. 2A shows a schematic structure of the substrate 100 in a dry state.
Figure 2B:
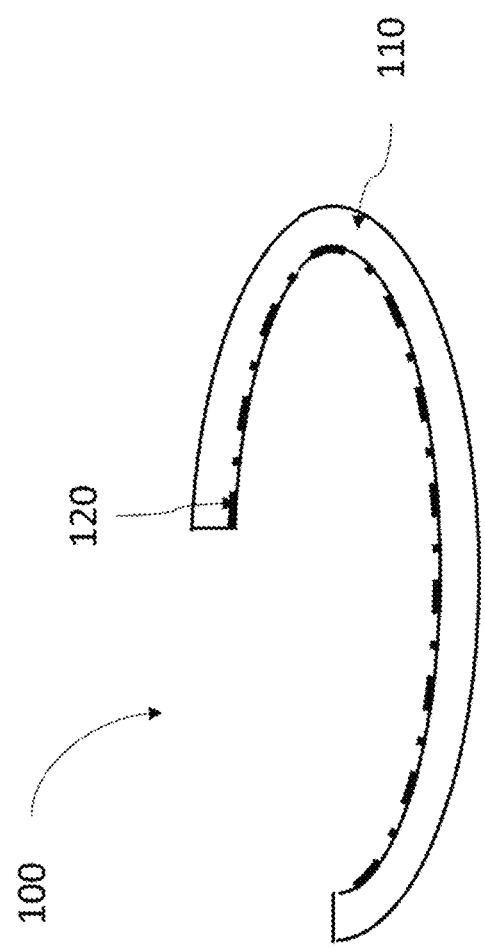
FIG. 2B shows a schematic structure of the substrate 100 in a wet state.

As stated above, the combination of the hygroexpansible material 110 and the hygroinert ink 120 may form a hygromorphic actuator. FIGS. 2A and 2B show a cross-section of a substrate 100 according to the first aspect or the second aspect after the user has used the writing instrument to draw on the substrate 100. As depicted in FIG. 2A the hygroinert ink 120 may be disposed on parts of the hygroexpansible material 110. As outlined above, the hygroexpansible material 110 may swell more compared to the hygroinert, thereby the substrate 100 may bend towards the hygroinert ink 120, as depicted in FIG. 2B. Further, the hygroinert ink 120, when dry, may be able to absorb tensile forces and/or tensile stress. In particular, the hygroinert ink 120 may have a higher Young's modulus compared to the hygroexpansible material 110. As a result, when the hygroexpansible material 110 expands, the hygroinert ink 120 may resist expanding to the same degree, resulting in the substrate 100 bending towards the hygroinert ink 120.

Hence, the combination of the hygroexpansible material 110 and hygroinert ink 120 may form a hygromorphic actuator due to at least two features. The hygroinert ink 120 may be configured to seal the hygroexpansible material 110 from a solvent, in particular water. Alternatively or additionally, the hygroinert ink 120 may form at least one hygroinert ink layer, in particular wherein the hygroinert ink layer is configured to absorb tensile forces. Alternatively or additionally, the hygroinert ink 120 may prevent water from penetrating into the hygroexpansible material 110 upon which the hygroinert ink 120 is disposed. As a result, only regions of the hygroexpansible material 110 upon which no hygroinert ink 120 is deposited swell, whereas regions whereupon the hygroinert ink 120 is deposited, do not swell. As a result, the substrate 100 may also bend towards the hygroinert ink 120.

The mechanism of the hygromorphic effect may be similar to that of a bimetallic strip, however whereas a bimetallic strip is configured to shape-shift when exhibiting to a change in temperature, the hygromorphic layer is configured to shape-shift when exhibiting a change in water content.

Figure 1A:
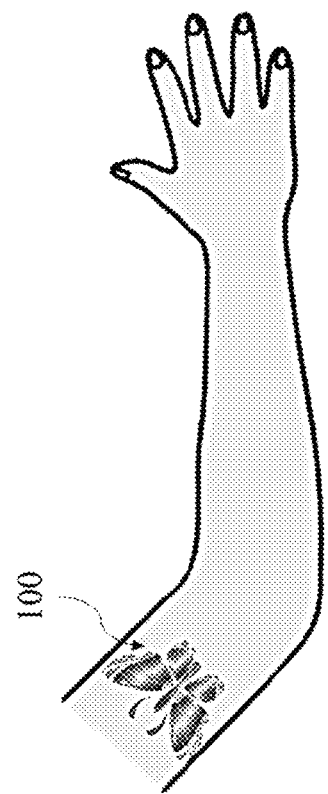
FIG. 1A shows a substrate according to the first aspect in a dry state attached to an arm.

FIGS. 1A and 1B shows an embodiment according to the first aspect. The substrate 100 according to the first aspect may, in some embodiments, be used as a sticker, in particular a sticker configured to be attached to human skin. FIGS. 1A and 1B show the substrate 100 attached to the upper arm of a user. The substrate 100 of FIGS. 1A and 1B is in the shape of a butterfly.

The substrate 100 according to the first aspect may be premanufactured. The substrate 100 according to the first aspect may be already provided in the shape of a butterfly and comprise the hygroinert ink 120 to perform the hygromorphic action.

The substrate 100 according to the second aspect may be in the shape of a butterfly or may be for example a square sheet, which is subsequently cut into shape by the user. The user may then add hygroinert ink 120 on the butterfly or parts thereof, depending on the desired hygromorphic action.

FIG. 1a shows the substrate 100, in particular the hygroexpansible material 110, in a dry state. Subsequently, the substrate 100 may absorb water. Sources of water may be for example sweat from the user, or water provided by an external device, such as a water spray mechanism. The substrate may also absorb water from ambient air. When the substrate 100, in particular the hygroexpansible material 110, absorbs water, it may perform its hygromorphic action. For example, the butterfly depicted in FIG. 1A, or parts thereof may unfold for a visual effect. FIG. 1B shows the substrate 100 in a wet state, wherein the wings of the butterfly have unfolded. The terms "dry state" and "wet state" are relative to one another, in particular the first structure may comprise more water relative to its total weight in the wet state, compared to its dry state.

In a substrate 100 according to the first aspect, which parts of the butterfly are unfolded may be determined by a predetermined arrangement of the hygroinert ink 120. In some embodiments, the hygroinert ink 120 may have been printed in a specific pattern onto the substrate 100, in particular the hygroexpansible material 110, such that the wings expand in a specific direction and/or to a specific degree.

In a substrate 100 according to the second aspect, the user may decide the pattern of the substrate 100 and thereby for example the specific direction and/or degree of the wings expanding.

The shape and color of the substrate 100 is not particularly limited. In some embodiments, instead of the butterfly, the substrate 100 may be shaped as a flower bud, which may unfold when water is absorbed by the substrate 100, in particular the hygroexpansible material 110.

Hygroexpansible Material

In some embodiments, the hygroexpansible material 110 may form a hygroexpansible layer and the hygroinert ink 120 may form a hygroinert layer, wherein the hygroinert layer may be disposed at least on a part of the hygroexpansible layer. The hygroinert ink 120 may form a plurality of layers. In some embodiments, additional layers may be placed between the hygroexpansible layer and the hygroinert layer.

The term "layer" within this disclosure may i.a. refer to its common meaning in the art. Additionally or alternatively, the term "layer" may refer to a structure, wherein the structure is greater in a first and second dimension compared to a third dimension, in particular wherein the first and second dimension are at least 3 times greater, more specifically at least 5 times greater and in particular at least 10 times greater than the first dimension. Additionally or alternatively, the term "layer" may refer to a structure wherein the structure has a continuous thickness, in particular wherein the thickness is the third dimension. The term "continuous thickness" may refer to at least 80% of the area defined by the first and second dimension having a variation of thickness in the third dimension of less than 30%, in particular less than 15%, relative to the mean thickness. It should be noted that a layer according to the aforementioned definition may comprise for example gaps in parts of the layer. The presence of gaps may, in some embodiments, improve the hygromorphic action.

The substrate 100 may also form a layer. The substrate 100 having two dimensions being greater than a third dimension may improve the hygromorphic actuation, as the resistance to bending may be low, compared to for example a substrate 100 wherein all dimensions are approximately the same, e.g. a sphere.

In some embodiments, the hygroinert ink 120 may cover between about 0.5% to about 100%, more specifically 1% to about 99%, even more specifically between about 5% to about 75% and in particular between about 20% to about 60% of the hygroexpansible material's 110 surface. If the hygroexpansible material 110 is in the form of a layer, the hygroinert ink 120 may cover between about 0.5% to about 100%, more specifically 1% to about 99%, even more specifically between about 5% to about 75% and in particular between about 20% to about 60% of the hygroexpansible layer's surface.

In some embodiments, the hygroexpansible material 110 may comprise a sporopollenin. In some embodiments, the hygroexpansible material 110 may comprise pollen paper. A hygroexpansible material 110 comprising pollen paper may show sufficient hygroexpansibility, while providing good mechanical properties, even when wet. Additionally, pollen paper may exhibit good properties for depositing ink thereon. Other hygroexpansible materials may be, in some instances, damaged by a writing instrument, in particular if the user exerts too much pressure. Further, pollen paper may allow depositing defined patterns of hygroinert ink thereon by printing. Further, pollen paper may be biodegradable.

As mentioned above, the hygroinert ink 120 may exhibit a higher Young's modulus compared to the hygroexpansible material 110. In some embodiments, the hygroexpansible material 110 may have a Young's modulus between about 90 to about 1200 MPa. In some embodiments, the hygroinert ink 120 may have a Young's modulus between about 5000 to about 20000, more specifically between about 10000 to about 12000. It should again be noted that the properties of the ink are defined in the state when it has dried on the substrate. In the writing instrument, the hygroinert ink may be a liquid or gel and may therefore exhibit a significantly lower Young's modulus.

In some embodiments, the substrate 100 may have a thickness between about 5 μm to about 1000 μm, more specifically between about 10 μm to about 100 μm. In some embodiments, the substrate 100 may have a diameter of between about 1 cm to about 100 cm.

In some embodiments, the substrate 100 may comprise a first section comprising the adhesive and a second section attached to the first section. In some embodiments, the first section may be attached to the second section in an attachment area.

In some embodiments, the second section may comprise a free end. In some embodiments, the second section may be a free end. The term "free end" may refer to a structure not specifically secured in a way that will effectively prevent its translation. Additionally or alternatively, the term "free end" may refer to a structure which may rotate and/or bend, in particular without a second structure being forced to rotate and/or bend with the structure. Additionally or alternatively, the term "free end" may refer to a structure configured to rotate when torque is applied, to bend when a lateral force is applied but not to translate, when a normal force pulling the "free end" away from the attachment area is applied. Additionally or alternatively, the term "free end" may refer to a structure configured to transfer torque, lateral forces and/or normal forces only in the attachment area. In some embodiments, the wings depicted in FIGS. 1A and 1B may be free ends, which may allow the wings to significantly lift off the underlying skin when water is absorbed by the hygroexpansible material 110.

In some embodiments, the second section may not comprise the adhesive. In the second section the hygroinert may be applied on both sides of the substrate 100. In some embodiments, the user may draw lines on both sides of the wings to obtain a wavy structure in the wings.

In some embodiments, the hygroexpansible material 110 may be configured to expand in at least one direction from about 0.4% to about 1.6%, when the water content within the hygroexpansible material 110 is increased from about 20 wt.-% to about 70 wt.-%.

In some embodiments, the substrate 100 may exhibit an increase of the maximum bending curvature of between about 1.0 cm$^{-1}$ to about 5.0 cm$^{-1}$, more specifically of between about 2.0 cm$^{-1}$ to about 4.0 cm$^{-1}$, and in particular of between about 2.5 cm$^{-1}$ to about 3.5 cm$^{-1}$, when a water content within the hygroexpansible material 110 is increased from about 20 wt.-% to about 100 wt.-%, relative to the maximum water absorption capacity of the hygroexpansible material 110. The maximum bending curvature may be achieved within up to 5 minutes, more specifically up to 3 min and in particular within 1 minute of exposure to water. The maximum bending curvature of the hygromorphic material may be the same as the maximum bending curvature of the substrate 100. Methods for determining the maximum bending curvature are known in the art. In some embodiments, the maximum bending curvature may be measured by taking images of the substrate 100, in particular a side-view of the substrate 100, at different water contents, in particular 20 wt.-% and 100 wt.-%, relative to the maximum water absorption capacity of the hygroexpansible material. The images may then be digitally analyzed by fitting a circle to the substrate's curvature. The reciprocal of the radius of the smallest circle fitted to the substrate's curvature may then be taken as the maximum bending curvature.

In some embodiments, the substrate 100 may have a deformability between about 0.02/cm*%-relative air humidity to about 0.25/cm*%-relative air humidity. The deformability may be defined as the maximum bending curvature divided by the relative air humidity at which the maximum bending curvature is achieved.

In some embodiments, the substrate 100 may have a deformability between about 0.02/cm*water content wt.-% to about 0.25/cm*water content wt.-%, wherein the water content is relative to the maximum water absorption capacity of the hygroexpansible material 110.

In some embodiments, the substrate 100 may exhibit an increase of the maximum bending curvature from about 0.10 cm$^{-1}$ to about 3.1 cm$^{-1}$ when the water content within the hygroexpansible material 110 is increased from about 20 wt.-% to about 100 wt.-%, relative to the maximum water absorption capacity of the hygroexpansible material 110.

Hygroinert Ink

In some embodiments, the hygroinert ink 120 may comprise a first polymer, more specifically a hydrocarbon polymer and in particular an aromatic hydrocarbon polymer. In some embodiments, the first polymer may comprise styrene, more specifically wherein the ink comprises a styrene acrylate copolymer and/or polystyrene. In some embodiments, the hygroinert ink 120 may comprise between about 10 wt.-% to about 100 wt.-%, more specifically between about 25 wt.-% to about 75 wt.-% and in particular between about 40 wt.-% to about 60 wt.-% of the first polymer. The first polymer may prevent water from passing therethrough and/or may not swell with water. Additionally, the first polymer may form a coherent structure, for example a layer, which may absorb tensile forces. Further, the first polymer may exhibit a higher Young's modulus compared to the hygroexpansible material 110.

In some embodiments, the hygroinert ink 120 may comprise alkyl ketene dimer.

In some embodiments, the hygroinert ink 120 may comprise between about 10 wt.-% to about 100 wt.-%, more specifically between about 25 wt.-% to about 75 wt.-% and in particular between about 40 wt.-% to about 60 wt.-% of the alkyl ketene dimer. Alkyl ketene dimers may impart hydrophobic properties to the hygroinert ink 120 and/or aid the hydrophobation of the underlying substrate 100, in particular the hygroexpansible material 110. The alkyl ketene dimers may seal the underlying hygroexpansible layer from water.

In some embodiments, the hygroinert ink 120 may comprise between about 10 wt.-% to about 99 wt.-%, more specifically between about 25 wt.-% to about wt.-% and in particular between about 40 wt.-% to about 60 wt.-% of p-xylene, when the ink is in the writing instrument. P-xylene may act as a solvent for the first polymer.

In some embodiments, the hygroinert ink 120 may comprise between about 2 wt.-% to about 90 wt.-%, more specifically between about 5 wt.-% to about wt.-% and in particular between about 10 wt.-% to about 20 wt.-% of one or more waxes. Waxes may impart hydrophobic properties to the hygroinert ink 120 and may seal the underlying hygroexpansible layer from water. Further, waxes may be immiscible with water, thus they may not swell with water.

In some embodiments, the hygroinert ink 120 may comprise water, propylene glycol, glycerin, amaranth and erioglaucine. For example, the hygroinert ink 120 may comprise 67 wt.-% water, 18 wt.-% propylene glycol, 10 wt.-% glycerin, 3.5 wt.-% amaranth, and 1.5 wt.-% erioglaucine, relative to the total weight of the hygroinert ink 120. The aforementioned ink composition may be skin safe and/or biodegradable.

In some embodiments, the hygroinert ink 120 may have a thickness between about 0.5 µm to about 50 µm, more specifically between about 2 µm to about 15 µm. In some embodiments, the hygroinert ink 120 may form one or more lines, wherein the one or more lines have a width between about 0.01 mm to about 10 mm, more specifically between about 0.1 mm to about 5 mm.

Mechanochromic Material

In the following, exemplary mechanochromic materials which may be comprised in substrate 100 according to the first aspect will be described in more detail.

As mentioned above, the substrate 100 may further comprise a mechanochromic material, in particular in the form of a mechanochromic layer 130. The mechanochromic layer 130 may have a thickness between about 1 µm to about 2000 µm, more specifically between about 5 µm to about 400 µm, and in particular between about 10 µm to about 200 µm.

Figure 3A:
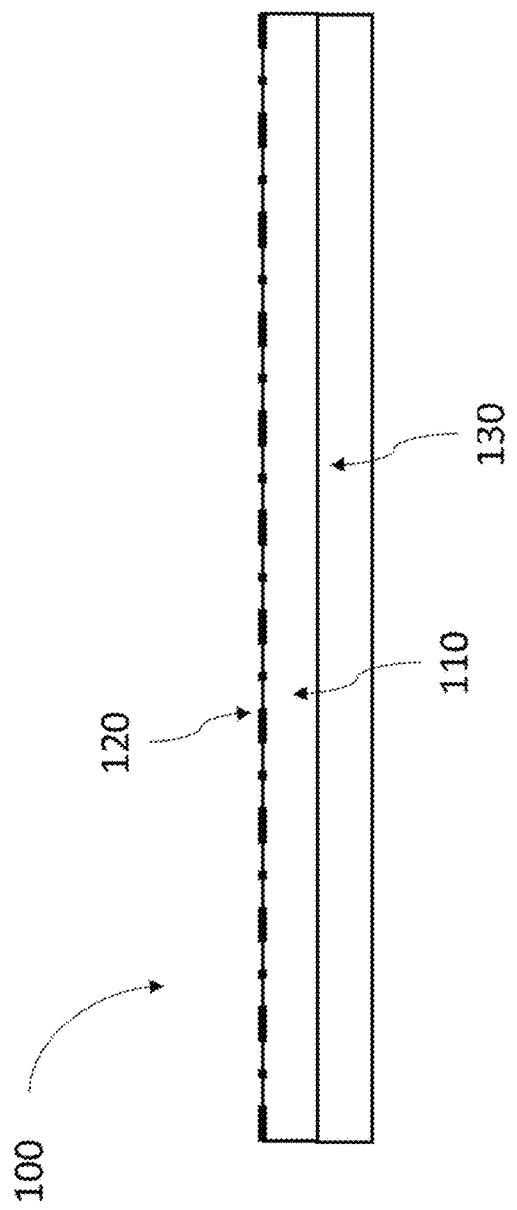
FIG. 3A shows a schematic structure of the substrate 100 comprising a mechanochromic layer 130 in a dry state.
Figure 3B:
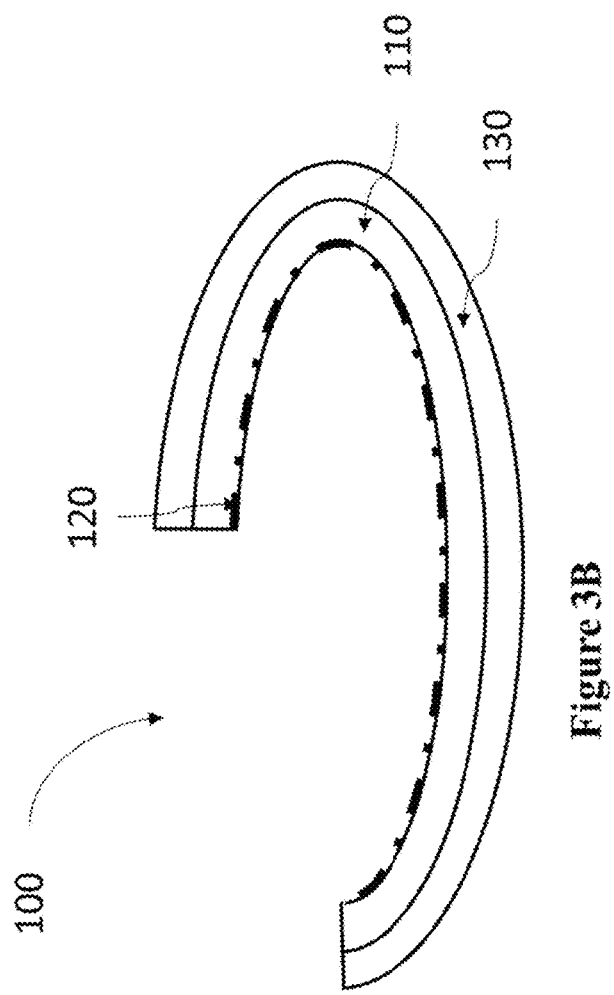
FIG. 3B shows a schematic structure of the substrate 100 comprising a mechanochromic layer 130 in a wet state.

In an embodiment, the hygroexpansible material 110 and the mechanochromic layer 130 may be arranged adjacent to one another, as depicted in FIG. 3A. In some embodiments, the mechanochromic layer 130 may be arranged on one side of the hygroexpansible material 110 and the hygroinert ink 120 applied on the other side of the hygroexpansible material 110. In some embodiments, in particular wherein the mechanochromic layer 130 allows water to pass therethrough, the mechanochromic layer 130 may be arranged on one side of the hygroexpansible material 110 and the hygroinert ink 120 applied on the mechanochromic layer 130. When the substrate 100 is bend due to the hygromorphic action, as depicted in FIG. 3B, stress and strain may be induced into the mechanochromic layer 130, which may lead to a color change of the mechanochromic layer 130.

In some embodiments, the mechanochromic material may comprise a photonic material, a piezophotonic material, a microcrack structure material and/or a mechanophore, in particular a mechanophore-linked polymer. The term "mechanophore" within this disclosure may i.a. refer to its common meaning in the art. Additionally or alternatively, the term "mechanophore" may relate to a molecule or molecular unit configured to change its color when exposed to stress or strain. Mechanophores may be in particular inserted or cross-linked into polymers or materials comprising polymers.

The mechanophore may be configured to undergo a ring-opening under mechanical stress, more specifically a reversible ring-opening under mechanical stress and in particular to transform from a ring-closed form, in a particular a spirocyclic form, to a ring-opened form under mechanical stress. The mechanophores may exhibit a first color or no color when in the ring-closed form and a second color when in the ring-opened form.

In some embodiments, the mechanochromic material may comprise mechanochromic fibers, in particular mechanochromic polymer fibers. In some embodiments, the mechanochromic fibers may comprise a spiropyran-functionalized polymer, in particular spiropyran-functionalized poly(methyl acrylate). The durability of the mechanochromic fibers may be improved by blending the spiropyran-functionalized polymer with another polymer, for example poly(methyl methacrylate). The spiropyran may act as a mechanophore and the polymer may be configured to transfer stress to the spiropyran.

Mechanochromic fibers are for example described in "Colaco et al., 2020, Mechanochromic Microfibers Stabilized by Polymer Blending, https://doi.org/10.1021/acsapm.0c00213", which is incorporated herein by reference.

In some embodiments, the mechanochromic material may comprise a mechanochromic polymer, more specifically a mechanochromic polymer comprising a rhodamine and in particular a mechanochromic rhodamine spirolactam micellar hydrogel. Rhodamines, in particular rhodamine spirolactams, may occur in a ring-closed form and a ring-opened form. The ring opening of some rhodamines, in particular rhodamine spirolactams may be force-induced, in particular stress-induced, hence rhodamine spirolactam may be a mechanophore. The polymer may transfer forces, in particular stress, to the rhodamine. In particular, the hydrogel may transfer forces into the micelles, wherein the micelles comprise rhodamine spirolactam. In some embodiments, the micelles may be formed of tween 80. The micelles may comprise an acrylate polymer. In particular, the acrylate polymer may cross-link the rhodamine within the micelles. In some embodiments, the hydrogel may be formed of an acrylamide polymer, and in particular the micelles may be cross-linked by the acrylamide polymer. When mechanical stress is applied to the hydrogel, the stress may be transferred to the micelles via the acrylate polymer. The micelles may deform due to the induced stress, leading to stress induced upon the acrylate polymer. The force induced on the acrylate polymer may be transferred to the rhodamines due to the cross-links between the rhodamines and the acrylate polymer, leading to a transformation of the rhodamine from the ring-closed state to the ring-opened state. Synthesis of a rhodamine spirolactam hydrogel is described in "Wang et al., 2018, Rhodamine-Functionalized Mechanochromic and Mechanofluorescent Hydrogels with Enhanced Mechanoresponsive Sensitivity, https://doi.org/10.3390/polym10090994", which is herein incorporated by reference.

In some embodiments, the mechanochromic material may comprise particles, in particular wherein the particles are spheres. More specifically the spheres may be polymer spheres and in particular the polymer spheres may comprise a copolymer of methyl methacrylate, butyl acrylate and methacrylic acid. In some embodiments, the particles may have a size between about 100 nm to about 400 nm, more specifically between about 200 nm to about 300 nm. In some embodiments, the mechanochromic material may comprise a latex. In particular, the particles described above may be present in the latex. The term "latex" within this disclosure may refer to emulsions of a polymer in a fluid, more specifically to an emulsion of polymer particles in water, and in particular an emulsion of polymer microparticles in water. The latex may be an elastic solid or a gel. More specifically the latex may comprise the polymer spheres and in particular the latex may comprise the polymer spheres and graphene. The graphene may be present in the form of graphene flakes comprising multiple layers of graphene. In some embodiments, the graphene may be exfoliated graphene flakes. In some embodiments, the graphene may have a size between about 150 nm to about 500 nm, more specifically between about 300 nm to about 400 nm in its greatest expansion. The latex may have a water content between about 1 wt.-% to about 30 wt.-%, more specifically between about 5 wt.-% to about 15 wt.-% and in particular between about 8 wt.-% to about 12 wt.-%, relative to the total weight of the latex. The latex may have undergone water evaporation to form a microstructure of colloidal crystals. The colloidal crystals may be formed of the polymer particles and may be enhanced by the graphene. The graphene may be trapped in the latex at the interstitial spaces between polymer particles and improve the assembly of the particles into colloidal crystals. The graphene may be replaced by graphene oxide. The term "colloidal crystal" within this disclosure may refer to an ordered array of colloid particles. The particles, in particular the polymer spheres, may be the colloid particles. The latex, in particular the colloidal crystals, may form a photonic material, in particular photonic crystals.

The term "photonic crystal" within this disclosure i.a. refers to its common meaning in the art. Additionally or alternatively the term "photonic crystal" may refer to a plurality of layers affecting the motion of light (photons), in particular a plurality of layers affecting the motion of light (photons) exhibiting a periodicity. Additionally or alternatively the term "photonic crystal" may refer to a plurality of layers having a photonic band-gap in at least one dimension.

Without wishing to be bound by theory, the photonic crystals may affect the motion of photons, in particular crystals may affect the motion of photons by exhibiting a photonic band-gap. The photonic band-gap allows light with a wavelength outside the photonic band-gap range to propagate through the plurality of layers, while light with a wavelength in the range of the photonic band-gap range cannot propagate. For light to be diffracted, the periodicity of a plurality of layers must correspond approximately to half of the wavelength of the light to be diffracted. The aforementioned layers may be formed by the aforementioned particles, in particular polymer spheres, wherein the particles are arranged to form a repeating structure, in particular a repeating layer structure. The photonic band-gap may therefore depend upon the periodicity of the layers or particles. When stress is induced into the latex, the distance between the particles, in particular the layer formed by the particles may change, in particular increase, which may change the photonic band gap, which again may change the color displayed by the latex. In some embodiments, the mechanochromic material may have a graphene content between about 0.001 wt.-% to about 0.1 wt.-%, more specifically between about 0.005 to about 0.02 wt.-% relative to the total weight of the polymer spheres.

A mechanochromic material comprising a latex comprising graphene is described in "Jurewicz et al., 2020, Mechanochromic and Thermochromic Sensors Based on Graphene Infused Polymer Opals, https://doi.org/10.1002/adfm.202002473", which is incorporated herein by reference.

The following mechanochromic materials may also form photonic crystals. The mechanochromic material may comprise silica particles and poly(ethylene glycol) phenyl ether acrylate rubber. The silica particles may be the particles described above. Alternatively or additionally, the mechanochromic material may comprise poly(butyl acrylate) spheres, 2-ethylhexyl acrylate and a polyacrylic acid hydrogel. The poly(butyl acrylate) spheres may be the polymer spheres referred to above. Additionally or alternatively, the mechanochromic material may comprise polystyrene spheres, at least one aligned carbon nanotubes sheet and PDMS fibers. The polystyrene spheres may be the polymer spheres referred to above.

In some embodiments, the color change of the mechanochromic material may be reversible. The color change being reversible, in particular in conjunction with the hygromorphic action being reversible may allow reusing the substrate 100.

In some embodiments, the mechanochromic material may be configured to change color when exposed to a mechanical force between about 0.1 N to about 5 N. In some embodiments, the mechanochromic material may be configured to change color when exposed to a mechanical force between about 0.3 MPa to about 3 MPa. The mechanical force may be in particular stress.

In some embodiments, the mechanochromic material may be configured to change color when stretched by between about 50% to about 500%. It should be noted, that the stretching of the mechanochromic material, may be greater than the expansion of the hygroexpansible material 110, due to the change in curvature of the substrate 100.

Adhesive

In some embodiments, the adhesive may be comprised within an adhesive layer. The term "adhesive" within this disclosure may refer to a structure configured to adhere to a surface of another structure. Additionally or alternatively, the term "adhesive" may refer to a curable fluid configured to bond a first and a second surface when cured. In some embodiments, a gel comprising polyvinylalcohol and borax may form a structure able to adhere to surfaces without additionally curing. On the other hand, liquid polyvinylalcohol may be used as a curable adhesive.

The adhesive may be safe for human use, in particular, if the substrate 100 is configured to be attached to human skin.

In some embodiments, the adhesive may be configured to be a removable adhesive. In some embodiments, the adhesive may comprise a material chosen from an acrylic, a rubber and/or a silicon.

In some embodiments, the adhesive may be attached to a detachable layer, more specifically a detachable layer comprising a polymer and in particular a detachable layer comprising cellulose paper, polypropylene and/or polyester The detachable layer may protect the adhesive from curing or from accumulating dirt, which may reduce the adhesive's adhesive properties. The detachable layer may then be peeled away before use. The substrate 100 comprising the detachable layer may allow the provision of a peel-away sticker. However, a detachable layer is not mandatory. In other embodiments, or additional to the detachable layer, the adhesive may be water activated. As a result, the adhesive may only exhibit its adhesive properties after contact with water.

In some embodiments, the substrate 100 may be a decal. The decal may be used to decorate, in some embodiments, plastic models. Alternatively, the decal may be used to decorate human skin.

Sealant

In some embodiments, the substrate 100 may comprise a sealant layer, more specifically a sealant layer configured to prevent water from passing therethrough. The sealant layer may be arranged between the adhesive and the hygroexpansible material 110 to prevent water from the user's skin to pass through towards the hygroexpansible material 110. The user may prefer to control when the hygromorphic action occurs, instead of the hygromorphic action occurring due to sweating or water evaporating from the user's skin.

In some embodiments, the sealant may comprise a fourth polymer, more specifically the sealant may comprise a biopolymer, and in particular the sealant may comprise chitosan.

Additional Layers

In some embodiments, the substrate 100 may comprise a base layer, more specifically wherein the base layer comprises a polymer and/or a paper, and in particular a biopolymer and/or a cellulose paper. The base layer may improve the mechanical properties of the substrate 100. Further, only parts of the hygromorphic material may be attached to the base layer. In some embodiments, the base layer may be fully in contact with user's skin, providing adhesion to the user. The hygromorphic material may be only attached to the base layer in certain areas and other parts of the hygromorphic layer may form one or more free ends (as detailed above). The base layer may be detachable, such that it only improves mechanical properties during storage and transport.

In some embodiments, the substrate 100 may comprise a water-absorbing material, in particular a hydrogel. The term "hydrogel" within this disclosure may refer to crosslinked hydrophilic polymers, in particular crosslinked hydrophilic polymers which do not dissolve in water. Hydrogels may absorb great amounts of water, e.g. up to 600 times their dry weight, while retaining defined structures. It should be noted, that within this disclosure, a hydrogel itself shall not fall under the term "hygromorphic actuator", as hydrogels typically only experience a change in volume and not in shape, e.g. curvature. The hydrogel may be comprised within the substrate 100 as the hygroexpansible material 110. The hydrogel may also be comprised within the substrate 100 in addition to a hygroexpansible material 110. As an addition, the hydrogel may act as a water reservoir, which may be configured to constantly supply the hygroexpansible material 110 with water, such that the duration of the shape change of the substrate is increased.

In some embodiments, the substrate 100 may comprise a middle layer attached to a top and a bottom layer, wherein the top layer is the sealant layer, the middle layer comprises the hygroexpansible material 110 and the hygroinert ink 120 and the bottom layer comprises the adhesive. The sealant layer attached to the top layer may prevent the hygroexpansible material from absorbing water unintentionally, for example during storage. The sealant layer attached to the top layer may result in the hygromorphic material absorbing water only from the user's skin. The sealant layer as the top layer may also be detachable, such that when the user wants to use the substrate 100, the user may remove the sealant layer.

As mentioned above, in some embodiments, the substrate 100 may comprise a detachable layer. The substrate 100 may comprise the detachable layer attached to the bottom layer, the porous layer arranged between the bottom layer and the middle layer and/or the base layer arranged between the bottom layer and the middle layer, in particular between the bottom layer and the porous layer.

In some embodiments, the substrate 100 may be a peel-away sticker.

In some embodiments, the substrate 100 may be configured to be attached to skin.

In a third aspect, the present disclosure relates to a method for manufacturing a substrate 100, wherein the method comprises adding an adhesive layer to a hygroexpansible material 110, in particular pollen paper. The process according to the third aspect may optionally comprise printing a pattern on the pollen paper with hygroinert ink 120.

In some embodiments, the process according to the third aspect comprises attaching a detachable layer to the adhesive layer and/or coating or attaching a sealant onto the pollen paper.

In a fourth aspect, the present disclosure relates to a kit comprising the substrate 100 or system according to any preceding embodiment, wherein the kit additionally comprises a water-spraying mechanism. In some embodiments, the water spraying mechanism may comprise a plain orifice spray nozzle, a flat fan spray pattern spray nozzle, a surface impingement spray nozzle or a spiral spray nozzle. The water spraying mechanism may be a spray bottle.

In a fifth aspect, the present disclosure relates to a use of the substrate 100 or system according to any preceding embodiment, wherein the substrate 100 is attached to skin.

In a sixth aspect, the present disclosure relates to a writing instrument according to any preceding embodiment.

In a seventh aspect, the present disclosure relates to an ink cartridge, wherein the ink cartridge comprises an ink as defined in any preceding embodiment, wherein the ink cartridge is configured to be inserted into the writing instrument or a printer.

The user may also design a pattern and print it on to a hygroexpansible material, to obtain a substrate according to the first aspect. As a result, in an eight aspect, the present disclosure also relates to a method for manufacturing the substrate according to the first aspect 100, wherein the method comprises:
  the user designing a pattern or selecting a pattern from a database,
  sending the pattern to a printer comprising the hygroexpansible material 110, in particular pollen paper, and the hygroinert ink 120, and
  the printer printing the pattern onto the hygroexpansible material 110 using the hygroinert ink 120.

The database may also show the expected deformation of the resulting substrate 100 for each pattern.

When designing the pattern himself, the user may be guided by a computer-implemented method. The computer-implemented method may comprise guiding the user in designing the pattern. Additionally or alternatively, the computer-implemented method may comprise visualizing an expected deformation of the resulting substrate 100 to the user.

Although the present disclosure is defined in the attached claims, it should be understood that the present disclosure can also (alternatively) be defined in accordance with the following aspects:

1. A substrate comprising:
   an adhesive,
   a hygroexpansible material, and
   a hygroinert ink.
2. A system comprising:
   a substrate comprising a hygroexpansible material and an adhesive;
   a writing instrument comprising an ink cartridge comprising a hygroinert ink.
3. The substrate or system according to any preceding aspect, wherein the hygroexpansible material is configured to swell and the hygroinert ink is configured not to swell.
4. The substrate or system according to any preceding aspect, wherein the hygroexpansible material is hydrophilic and the hygroinert ink is hydrophobic.
5. The substrate or system according to any preceding aspect, wherein the hygroexpansible material forms a hygroexpansible layer and the hygroinert ink forms a hygroinert layer, wherein the hygroinert layer is disposed at least on a part of the hygroexpansible layer.
6. The substrate or system according to any preceding aspect, wherein the hygroinert ink covers between about 0.5% to about 100%, more specifically about 1% to about 99%, even more specifically between about 5% to about 75% and in particular between about 20% to about 60% of the hygroexpansible material's or hygroexpansible layer's surface.
7. The substrate or system according to any preceding aspect, wherein the hygroexpansible material comprises a sporopollenin.
8. The substrate or system according to any preceding aspect, wherein the hygroexpansible material comprises pollen paper.
9. The substrate or system according to any preceding aspect, wherein the hygroexpansible material has a Young's modulus between about 90 to about 1200 MPa.
10. The substrate or system according to any preceding aspect, wherein the hygroinert ink has a Young's modulus between about 5000 to about 20000, more specifically between about 10000 to about 12000, when dry.
11. The substrate or system according to any preceding aspect, wherein the substrate has a thickness between about 5 μm to about 1000 μm, more specifically between about 10 μm to about 100 μm.
12. The substrate or system according to any preceding aspect, wherein the substrate has a diameter of between about 1 cm to about 100 cm.
13. The substrate or system according to any preceding aspect, wherein the substrate comprises a first section comprising the adhesive and a second section attached to the first section.
14. The substrate or system according to any preceding aspect, wherein the first section is attached to the second section in an attachment area.
15. The substrate or system according to aspect 13 or 14, wherein the second section does not comprise the adhesive.
16. The substrate or system according to any one of aspects 13 to 15, wherein the second section comprises a free end.
17. The substrate or system according to any one of aspects 13 to 15, wherein the second section is a free end.
18. The substrate or system according to any preceding aspect, wherein the hygroexpansible material is configured to expand in at least one direction from about 0.4% to about 1.6%, when the water content within the hygroexpansible material is increased from about 20 wt.-% to about 70 wt.-%.
19. The substrate or system according to any preceding aspect, wherein the substrate has a deformability between about 0.02/cm*%-relative air humidity to about 0.25/cm*%-relative air humidity.
20. The substrate or system according to any preceding aspect, wherein the substrate has a deformability between about 0.02/cm*water content wt.-% to about 0.25/cm*water content wt.-%, wherein the water content is relative to the maximum water absorption capacity of the hygroexpansible material.
21. The substrate or system according to any preceding aspect, wherein the substrate exhibits an increase of the maximum bending curvature of between about 1.0 cm$^{-1}$ to about 5.0 cm$^{-1}$, more specifically of between about 2.0 cm$^{-1}$ to about 4.0 cm$^{-1}$, and in particular of between about 2.5 cm$^{-1}$ to about 3.5 cm$^{-1}$, when a water content within the hygroexpansible material is increased from about 20 wt.-% to about 100 wt.-%, relative to the maximum water absorption capacity of the hygroexpansible material.
22. The substrate or system according to any preceding aspect, wherein the substrate exhibits an increase of the maximum bending curvature from about 0.10 cm$^{-1}$ to about 3.1 cm$^{-1}$ when the water content within the hygroexpansible material is increased from about 20 wt.-% to about 100 wt.-%, relative to the maximum water absorption capacity of the hygroexpansible material.
23. The substrate or system according to any preceding aspect, wherein the hygroinert ink is configured to seal the hygroexpansible material from a solvent, in particular water.
24. The substrate or system according to any preceding aspect, wherein the hygroinert ink forms at least one hygroinert ink layer, in particular wherein the hygroinert ink layer is configured to absorb tensile forces.
25. The substrate or system according to any preceding aspect, wherein the hygroinert ink comprises a first polymer, more specifically a hydrocarbon polymer and in particular an aromatic hydrocarbon polymer.
26. The substrate or system according to aspect 25, wherein the first polymer comprises styrene, more specifically wherein the ink comprises a styrene acrylate copolymer and/or polystyrene.
27. The substrate or system according to any preceding aspect, wherein the hygroexpansible material comprises a sporopollenin, more specifically pollen paper, and the hygroinert ink comprises an aromatic hydrocarbon polymer, more specifically a styrene acrylate copolymer and/or polystyrene.
28. The substrate or system according to aspect 25 to 27, wherein the hygroinert ink comprises between about 10 wt.-% to about 100 wt.-%, more specifically between about 25 wt.-% to about 75 wt.-% and in particular between about 40 wt.-% to about 60 wt.-% of the first polymer.
29. The substrate or system according to any preceding aspect, wherein the hygroinert ink comprises alkyl ketene dimer, in particular wherein the hygroinert ink comprises between about 10 wt.-% to about 100 wt.-%, more specifically between about 25 wt.-% to about 75 wt.-% and in particular between about 40 wt.-% to about 60 wt.-% of the alkyl ketene dimer.

30. The substrate or system according to any preceding aspect, wherein the hygroinert ink comprises p-xylene in particular wherein the hygroinert ink comprises between about 10 wt.-% to about 99 wt.-%, more specifically between about 25 wt.-% to about 75 wt.-% and in particular between about 40 wt.-% to about 60 wt.-% of p-xylene.

31. The substrate or system according to any preceding aspect, wherein the hygroinert ink comprises between about 2 wt.-% to about 90 wt.-%, more specifically between about 5 wt.-% to about 50 wt.-% and in particular between about 10 wt.-% to about 20 wt.-% of one or more waxes.

32. The substrate or system according to any preceding aspect, wherein the hygroinert ink has a thickness between about 0.5 μm μm to about 50 μm more specifically between about 2 μm to about 15 μm.

33. The substrate or system according to any preceding aspect, wherein the hygroinert ink forms one or more lines, wherein the one or more lines have a width between about 0.01 mm to about 10 mm, more specifically between about 0.1 mm to about 5 mm.

34. The substrate or system according to any preceding aspect, wherein the substrate further comprises a mechanochromic material, in particular in the form of a mechanochromic layer.

35. The substrate or system according to aspect 34, wherein the mechanochromic material comprises mechanochromic fibers, in particular mechanochromic polymer fibers.

36. The substrate or system according to aspect 34 or 35, wherein the mechanochromic layer has a thickness between about 1 μm to about 2000 μm, more specifically between about 5 μm to about 400 μm, and in particular between about 10 μm to about 200 μm.

37. The substrate or system according to any one of aspects 34 to 36, wherein the mechanochromic material comprises a photonic material, a piezophotonic material, a microcrack structure material and/or a mechanophore, in particular a mechanophore-linked polymer.

38. The substrate or system according to aspect 37, wherein the mechanophore is configured to undergo a ring-opening under mechanical stress, more specifically a reversible ring-opening under mechanical stress and in particular to transform from a spirocyclic form to a ring-opening form under mechanical stress.

39. The substrate or system according to any one of aspects 34 to 38, wherein the mechanochromic material comprises a mechanochromic polymer, more specifically a mechanochromic polymer comprising a rhodamine and in particular a mechanochromic rhodamine spirolactam micellar hydrogel.

40. The substrate or system according to any one of aspects 34 to 39, wherein the mechanochromic material comprises spheres, more specifically wherein the spheres are polymer spheres and in particular wherein the polymer spheres comprise a copolymer of methyl methacrylate, butyl acrylate and methacrylic acid.

41. The substrate or system according to any one of aspects 34 to 40, wherein the mechanochromic material comprises a latex, more specifically wherein the latex comprises the polymer spheres and in particular wherein the latex comprises the polymer spheres and graphene.

42. The substrate or system according to aspect 41, wherein the polymer spheres have a size between about 100 nm to about 400 nm, more specifically between about 200 nm to about 300 nm.

43. The substrate or system according to any one of aspects 34 to 42, wherein the mechanochromic material has a graphene content between about 0.001 wt.-% to about 0.1 wt.-%, more specifically between about 0.005 to about 0.02 wt.-% relative to the total weight of the polymer spheres.

44. The substrate or system according to any one of aspects 41 to 43, wherein the latex has a water content between about 1 wt.-% to about 30 wt.-%, more specifically between about 5 wt.-% to about 15 wt.-% and in particular between about 8 wt.-% to about 12 wt.-%, relative to the total weight of the latex.

45. The substrate or system according to any one of aspects 34 to 44, wherein the mechanochromic material comprises silica particles and poly(ethylene glycol) phenyl ether acrylate rubber.

46. The substrate or system according to any one of aspects 34 to 45, wherein the mechanochromic material comprises polystyrene spheres, at least one aligned carbon nanotubes sheet and PDMS fibers.

47. The substrate or system according to any one of aspects 34 to 46, wherein the mechanochromic material comprises poly(butyl acrylate) spheres, 2-ethylhexyl acrylate and a polyacrylic acid hydrogel.

48. The substrate or system according to any one of aspects 34 to 47, wherein a color change of the mechanochromic material is reversible.

49. The substrate or system according to any one of aspects 34 to 48, wherein the mechanochromic material is configured to change color when exposed to a mechanical force between about 0.1 N to about 5 N.

50. The substrate or system according to any one of aspects 34 to 49, wherein the mechanochromic material is configured to change color when stretched by between about 50% to about 500%.

51. The substrate or system according to any one of aspects 34 to 50, wherein the mechanochromic material is configured to change color when exposed to a mechanical force between about 0.3 MPa to about 3 MPa.

52. The substrate or system according to any preceding aspect, wherein the adhesive is comprised within an adhesive layer.

53. The substrate or system according to any preceding aspect, wherein the adhesive is safe for human use.

54. The substrate or system according to any preceding aspect, wherein the adhesive is configured to be a removable adhesive.

55. The substrate or system according to any preceding aspect, wherein the adhesive comprises a second polymer, in particular an acrylic, a rubber and/or a silicon.

56. The substrate or system according to any preceding aspect, wherein the adhesive is attached to a detachable layer, more specifically a detachable layer comprising a third polymer and in particular a detachable layer comprising cellulose paper, polypropylene and/or polyester.

57. The substrate or system according to any preceding aspect, wherein the substrate comprises a sealant layer, more specifically a sealant layer configured to prevent water from passing therethrough.

58. The substrate or system according to aspect 57, wherein the sealant comprises a fourth polymer, more specifically wherein the sealant comprises a biopolymer, and in particular wherein the sealant comprises chitosan.
59. The substrate or system according to any preceding aspect, wherein substrate comprises a base layer, more specifically wherein the base layer comprises a polymer and/or paper, and in particular a biopolymer and/or cellulose paper.
60. The substrate or system according to any preceding aspect, wherein the substrate comprises a water-absorbing material, in particular a hydrogel.
61. The substrate or system according to any preceding aspect, wherein the substrate comprises a middle layer attached to a top and a bottom layer, wherein the top layer is the sealant layer, the middle layer comprises the hygroexpansible material and the hygroinert ink and the bottom layer comprises the adhesive.
62. The substrate or system according to aspect 61, wherein the substrate additionally comprises the detachable layer attached to the bottom layer and the base layer arranged between bottom layer and the middle layer.
63. The substrate or system according to any preceding aspect, wherein the substrate is a decal.
64. The substrate or system according to any preceding aspect, wherein the substrate is configured to be attached to skin.
65. A method for manufacturing a substrate, wherein the method comprises:
    adding an adhesive layer to a hygroexpansible material, in particular pollen paper,
    (optionally) printing a pattern on the hygroexpansible material with hygroinert ink.
66. The method according to aspect 65, wherein the process comprises:
    attaching a detachable layer to the adhesive layer and/or,
    coating or attaching a sealant onto the hygroexpansible material.
67. A kit comprising the substrate or system according to any one of aspects 1 to 64, wherein the kit additionally comprises a water-spraying mechanism.
68. Use of the substrate or system according to any one of aspects 1 to 64, wherein the substrate is attached to skin.
69. A writing instrument according to any one of aspects 2 to 64.
70. An ink cartridge, wherein the ink cartridge comprises an ink as defined in any one of aspects 1 to 64, wherein the ink cartridge is configured to be inserted into the writing instrument or a printer.

The invention claimed is:

1. A substrate comprising:
an adhesive,
a hygroexpansible material,
a hygroinert ink,
wherein the hygroexpansible material is hydrophilic and the hygroinert ink is hydrophobic and wherein the hygroexpansible material forms a hygroexpansible layer and the hygroinert ink forms a hygroinert layer, wherein the hygroinert layer is disposed at least on a part of the hygroexpansible layer, and wherein the adhesive is comprised within an adhesive layer;
wherein the substrate comprises a first section comprising the adhesive, and a second section attached to the first section,
wherein the second section comprises a free end.

2. A system comprising:
a substrate comprising a hygroexpansible material, an adhesive;
a writing instrument comprising an ink cartridge comprising a hygroinert ink,
wherein the hygroexpansible material is hydrophilic and the hygroinert ink is hydrophobic, and wherein the adhesive is comprised within an adhesive layer,
wherein the substrate comprises a first section comprising the adhesive, and a second section attached to the first section,
wherein the second section comprises a free end.

3. The substrate according to claim 1, wherein the hygroexpansible material is configured to swell and the hygroinert ink is configured not to swell.
4. The substrate according to claim 1, wherein the hygroinert ink covers between about 0.5% to about 100% of a hygroexpansible material's surface.
5. The substrate according to claim 1, wherein the hygroexpansible material comprises a sporopollenin.
6. The substrate according to claim 1, wherein the hygroexpansible material comprises pollen paper.
7. The substrate according to claim 1, wherein the hygroexpansible material has a Young's modulus between about 90 to about 1200 MPa.
8. The substrate according to claim 1, wherein the hygroinert ink has a Young's modulus between about 5000 to about 20000 MPa, when dry.
9. The substrate according to claim 1, wherein the hygroinert ink is configured to seal the hygroexpansible material from a solvent.
10. The substrate according to claim 9, wherein the solvent is water.
11. The substrate according to claim 1, wherein the hygroinert ink forms at least one hygroinert ink layer.
12. The substrate according to claim 11, wherein the hygroinert ink layer is configured to absorb tensile forces.
13. The substrate according to claim 1, wherein the hygroinert ink comprises a first polymer which is a hydrocarbon polymer.
14. The substrate according to claim 13, wherein the first polymer is an aromatic hydrocarbon polymer.
15. The substrate according to claim 13, wherein the first polymer is a styrene acrylate copolymer and/or polystyrene.
16. The substrate according to claim 1, further comprising a mechanochromic material.
17. The substrate according to claim 13, wherein the hygroexpansible material comprises a sporopollenin and/or wherein the first polymer is a styrene acrylate copolymer and/or polystyrene.

* * * * *

UNITED STATES PATENT AND TRADEMARK OFFICE
CERTIFICATE OF CORRECTION

| | | |
|---|---|---|
| PATENT NO. | : 12,324,851 B2 | Page 1 of 1 |
| APPLICATION NO. | : 18/325820 | |
| DATED | : June 10, 2025 | |
| INVENTOR(S) | : Nikolaos Chrysanthakopoulos | |

It is certified that error appears in the above-identified patent and that said Letters Patent is hereby corrected as shown below:

On the Title Page

After "US 2023/0381089 A1 Nov. 30, 2023" insert:
--(30) Foreign Application Priority Data
May 31, 2022 (EP) ...................................... 22176489--.

Signed and Sealed this
Twenty-ninth Day of July, 2025

Coke Morgan Stewart
*Acting Director of the United States Patent and Trademark Office*